US009457078B2

(12) United States Patent
Staffler et al.

(10) Patent No.: US 9,457,078 B2

(45) Date of Patent: Oct. 4, 2016

(54) METHODS FOR INHIBITING C5A WITH C5A PEPTIDES COUPLED OR FUSED TO A CARRIER PROTEIN

(75) Inventors: Guenther Staffler, Vienna (AT); Christine Landlinger, Vienna (AT); Frank Mattner, Vienna (AT)

(73) Assignee: AFFIRIS AG, Vienna (AT)

( * ) Notice: Subject to any disclaimer, the term of this patent is extended or adjusted under 35 U.S.C. 154(b) by 216 days.

(21) Appl. No.: 13/879,740

(22) PCT Filed: Dec. 21, 2011

(86) PCT No.: PCT/EP2011/073599

§ 371 (c)(1),
(2), (4) Date: Apr. 16, 2013

(87) PCT Pub. No.: WO2012/085090

PCT Pub. Date: Jun. 28, 2012

(65) Prior Publication Data

US 2013/0216565 A1 Aug. 22, 2013

(30) Foreign Application Priority Data

Dec. 21, 2010 (EP) .................................... 10196232

(51) Int. Cl.

*A61K 38/04* (2006.01)
*A61K 39/385* (2006.01)
*A61K 39/00* (2006.01)
*C07K 14/47* (2006.01)

(52) U.S. Cl.

CPC ......... *A61K 39/385* (2013.01); *A61K 39/0005* (2013.01); *A61K 39/0007* (2013.01); *A61K 39/0008* (2013.01); *C07K 14/472* (2013.01); *A61K 2039/55505* (2013.01); *A61K 2039/6081* (2013.01)

(58) Field of Classification Search

None

See application file for complete search history.

(56) References Cited

U.S. PATENT DOCUMENTS

| | | | | |
|---|---|---|---|---|
| 6,465,614 | B1 * | 10/2002 | Sanderson et al. | 530/328 |
| 6,821,950 | B1 * | 11/2004 | Fairlie et al. | 514/16.6 |
| 7,538,211 | B2 * | 5/2009 | Benedict et al. | 536/24.5 |
| 2002/0165138 | A1 * | 11/2002 | Ward et al. | 514/12 |
| 2010/0111995 | A1 | 5/2010 | Bachman et al. | |

FOREIGN PATENT DOCUMENTS

| | | | |
|---|---|---|---|
| CN | 101193654 | A | 6/2008 |
| JP | 2006-507834 | | 3/2006 |
| WO | WO 90/09162 | A2 | 8/1990 |
| WO | WO 2006/134125 | A1 | 12/2006 |

OTHER PUBLICATIONS

Written Opinion of the International Search Authority in PCT/EP11/073599 (Jun. 21, 2013).*
Shen et al., Translational Neurodegeneration 2: 1-11, 2013.*
Sabharwal et al., Chin. J. Contemp Neurosurg 14: 139-151, 2014.*
Kola et al., Immunotechnology 2: 115-126, 1996.*
Kawatsu et al., Journal of Pharmacology and Experimental Therapeutics 278: 432-440, 1996.*
Fonseca et al., Journal of Immunology 183: 1375-1383, 2009.*
Office Action issued Mar. 31, 2014 in Chinese Patent Application No. 201180061862.X (submitting English language translation only).
International Search Report issued May 31, 2012 in PCT/EP2011/073599 submitting English translation only.
Do-Yeun Kim, et al., "Expression of complement protein C5a in a murine mammary cancer model: tumor regression by interference with the cell cycle", Cancer Immunology Immunotherapy, XP19333071A, vol. 54, No. 10, 2005, pp. 1026-1037.
Kutty Selva Nandakumar, et al., "A Recombinant Vaccine Effectively Induces C5a-Specific Neutralizing Antibodies and Prevents Arthritis", PLOS One, XP2637243A, vol. 5, No. 10, Oct. 2010, pp. 1-11.
Or Y S, et al., "Improvements in the Minimum Binding Sequence of C5a: Examination of His-67", Journal of Medicinal Chemistry, XP2671362, vol. 35, No. 2, 1992, pp. 402-406.
Vladimir M. Pisarev, et al., "T cells recognize PD(N/T)R motif common in a variable number of tandem repeat and degenerate repeat sequences of MUC1", International Immunopharmacology, XP4713752A, vol. 5, No. 2, 2005, pp. 315-330.
Anthony A. Floreani, et al., "Novel C5a Agonist-Based Dendritic Cell Vaccine in a Murine Model of Melanoma", Cell Cycle, XP2637244A, vol. 6, No. 22, Nov. 15, 2007, pp. 2835-2839.
Sam D. Sanderson, et al. "Immunization to nicotine with a peptide-based vaccine composed of a conformationally biased agonist of C5a as a molecular adjuvant", International Immunopharmacology, XP2637245A, vol. 3, No. 1, 2003, pp. 137-146.
Sam D. Sanderson, et al., "Decapeptide Agonists of Human C5a: The Relationship between Conformation and Spasmogenic and Platelet Aggregatory Activities", Journal of Medicinal Chemistry, XP1156477A, vol. 37, No. 19, 1994, pp. 3171-3180.
Julia A. Ember, et al., "Biologic Activity of Synthetic Analogues of C5a Anaphylatoxin", American Association of Immunologists, XP1156478A, vol. 148, No. 10, May 15, 1992, pp. 3165-3173.
Megumi Kawai, et al., "Identification and Synthesis of a Receptor Binding Site of Human Anaphylatoxin", Journal of Medicinal Chemistry, XP2637256A, vol. 34, No. 7, 1991, pp. 2068-2071.

(Continued)

*Primary Examiner* — Phillip Gambel

(74) *Attorney, Agent, or Firm* — Oblon, McClelland, Maier & Neustadt, L.L.P.

(57) ABSTRACT

The present invention relates to a vaccine comprising at least one peptide consisting of amino acid sequence LRANISH-KDMQLGR (SEQ ID No. 1) or a peptide fragment thereof (SEQ ID No. 2-13) coupled or fused to a carrier protein comprising at least one T cell epitope, wherein said peptide fragment comprises at least 7 amino acid residues and the amino acid sequence KDMQLGR (SEQ ID No: 7) or KDMQLG (SEQ ID No: 23) under the provision that the peptide fragment does not consist of amino acid sequences HKDMQLGR (SEQ ID No: 16) and HKDMQLG (SEQ ID No: 22).

15 Claims, 3 Drawing Sheets

(56) References Cited

OTHER PUBLICATIONS

Y. Kaneko, et al., “Antagonistic peptides against human anaphylatoxin C5a”, Immunology, XP523705A, vol. 86, No. 1, Sep. 1995, pp. 149-154.
Ines J. Laudes, et al., “Anti-C5a Ameliorates Coagulation/Fibrinolytic Protein Changes in a Rat Model of Sepsis”, The American Journal of Pathology, XP2637247A, vol. 160, No. 5, May 2002, pp. 1867-1875.
Search Report and Written Opinion issued Aug. 4, 2014 in Singaporean Patent Application No. 2013025804.
Ganapati V. Hegde, et al., “A conformationally-biased, response-selective agonist of C5a acts as a molecular adjuvant by modulating antigen processing and presentation activities of human dendritic cells”, International Immunopharmacology, vol. 8, Jan. 30, 2008, pp. 819-827.
Edward L. Morgan, et al., “Enhancement of In Vivo and In Vitro immune functions by a conformationally-biased, response-selective agonist of human C5a: Implications for a novel adjuvant in vaccine design”, Vaccine, vol. 28, No. 2, Dec. 11, 2009, pp. 1-17.
Office Action issued Oct. 13, 2015 in Japanese Patent Application No. 2013-545364 (with English translation).
J. Köhl, et. al., “Evaluation of the C-terminal C5a effector site with short synthetic C5a analog peptides”, Eur. J. Immunol., 1993, vol. 23, pp. 646-652.
Feng Ni, et al., “Stabilization of an Isolated Helical Capping Box in Solution by Hydrophobic Interactions: Evidence from the NMR Study of Bioactive Peptides from the C-Terminus of Human C5a Anaphylatoxin”, Biopolymers, 1996, vol. 38, pp. 31-41.
Axel Kola, et al., “Epitope mapping of a C5a neutralizing mAb using a combined approach of phage display, synthetic peptides and site-directed Mutagenesis”, Immunotechnology, 1996, vol. 2, pp. 115-126.

* cited by examiner

METHODS FOR INHIBITING C5A WITH C5A PEPTIDES COUPLED OR FUSED TO A CARRIER PROTEIN

This application is a National Stage of PCT/EP11/073599 filed Dec. 21, 2011 and claims the benefit of EP 10 196 232.2 filed Dec. 21, 2010.

The present invention relates to a medicament to be used in the fields of medicine, immunology, and molecular biology to prevent and/or treat complement component C5a induced chronic inflammatory diseases.

The complement is a central component of the innate immune system, acting to protect the host from microorganism such as viruses, bacteria, and other foreign and abnormal cells. However, inappropriate or excessive activation of the complement system can lead to destructive capabilities against the host itself. Uncontrolled complement activation is involved in a number of neurodegenerative diseases such as Alzheimer's disease, Parkinson's disease and Huntington's disease; in chronic inflammatory diseases including age-related macula degeneration, rheumatoid arthritis, systemic lupus erythematosus (SLE), antiphospholipid syndrome (APS), asthma, vasculitis, atherosclerosis, multiple sclerosis, inflammatory dermatitis such as psoriasis and chronic urticaria, Guillain-Barre syndrome, and hemolytic uremic syndrome.

Uncontrolled complement activation can also occur in cancer, in pregnancy complications such as preeclamsia and APS, under acute pathological conditions including sepsis, acute lung injury, acute respiratory distress syndrome (ARDS), ischemia-reperfusion injury, and on artificial surfaces leading to hemodialysis-associated thrombosis.

Many of the toxic effects seen in these conditions are attributable to the excessive production of the anaphylatoxin C5a which promotes and perpetuates inflammatory reactions. The main function of C5a is chemotaxis and activation of granulocytes, mast cells, and macrophages to release soluble immune mediators. Inhibition or modulation of complement activity has therefore been recognized as a promising therapeutic strategy for many years.

Most complement proteins exist in plasma as inactive precursors that cleave and activate each other in a proteolytic cascade in response to three different mechanisms: the classical pathway, the lectin-induced, and the alternative pathway. The final result of all three activation cascades is massive amplification of the response and formation of the anaphylatoxins C3a and C5a and the cell-killing membrane attack complex (MAC), a pore causing lysis of cells.

The classical pathway is mainly activated by antigen-antibody complexes. When the intact macromolecular C1 protein binds to the exposed regions of at least two antigen-bound antibodies, the C1r and C1s subunits are activated. Activated C1s is responsible for the cleavage of the next two involved complement components, C4 and C2. C4 is cleaved into two fragments. The larger C4b molecule attaches to the target membrane nearby while the small C4a molecule floats away. Again, activated C1s cleaves the C2 molecule, yielding C2b and C2a, whereat the latter is released. What remains bound to the membrane is C4b2a, also known as the C3 convertase, which converts the next complement component, C3, into its active form. The C3 convertase splits multiple C3 into the larger C3b and the smaller C3a fragments. C5 convertase is then formed by assembly of the heterotrimeric complex, C4b2a3b, which catalyzes the cleavage of hundreds to thousands of C5 complement component into C5a and C5b before it reverts to inactivity. C5a floats away and contributes to inflammation while the C5b fragment binds to the antigen surface initiating the formation of the membrane attack complex (MAC).

The second complement activation pathway is the lectin-binding pathway. This pathway is triggered by binding mannose-binding lectin (MBL) or ficolins to mannose residues on the pathogen surface, which activates the MBL-associated serine proteases, MASP-1, and MASP-2. MASPs can then split C4 into C4a and C4b and C2 into C2a and C2b, leading to the formation of the classical pathway C3 and C5 convertases.

The alternative pathway is directly initiated by surface molecules containing carbohydrates and lipids of pathogens. The complement component C3 is spontaneously cleaved at low levels. The C3b component can attach to a number of different surfaces, both foreign and host cells alike. C3b is quickly inactivated by the sialic acid found on most mammalian cell surfaces. Microbes, most of which lack sialic acid, are stable sites for C3b deposition. Membrane-bound C3b fragments are bound by Factor B which is, in turn, cleaved by Factor D. The fragment Ba is released, while Bb stays associated with C3b. The resulting C3bBb molecule is the alternative pathway C3 convertase. The C3b molecule remains attached to form the alternative pathway C5 convertase, C3bBb3b. This enzyme cleaves C5 into C5a and C5b. The C5b molecule remains associated with the membrane and associates with C6 through C9 to form the MAC, whereas C5a acts as anaphylatoxin.

The complement component C5 is a 190 kDa protein and comprises two chains (α 115 kDa and β 75 kDa). Activation of either complement pathway can generate a C5 convertase enzyme capable of cleaving C5 to C5b and the potent anaphylatoxin C5a. Upon cleavage of C5 a C-terminal neoepitope on the C5a fragment is formed.

Human C5a is a 74-amino acids glycoprotein with the molecular weight of 12-14.5 kDa. An asparagine is located at position 64 which has an N-linked carbohydrate moiety that is not essential for biological activity but very likely regulates C5a activity in vivo. NMR spectroscopy showed an anti-parallel four helices bundle, the four different helical segments being stabilized by three disulphide bonds and connected by loop segments. On the N-terminus a short 1.5 turn helix is also present. C5a binds to two seven-transmembrane domain receptors, C5aR (CD88) and C5L2 (gpr77), which are ubiquitously expressed on a wide variety of cells but particularly on the surface of immune cells like macrophages, neutrophils, mast cells, and T cells. The ligand-binding site of C5aR is complex and consists of at least two physically separable binding domains. One binds the C5a disulfide-linked core (amino acids 15-46), while the second binds the C5a carboxy-terminal end (amino acid 67-74). The binding affinity of C5aR to its ligand C5a is very high, indicating a dissociation constant ($K_D$) of about 1 nM. However, C5a is rapidly metabolized by serum and cell surface carboxy-peptidases to a 73 amino acid form, C5a desArg, whereat the binding affinity to C5aR is decreased 10 to 100-fold.

Rabbit polyclonal antibodies were developed to three peptide regions of rat C5a, the N-terminal region residues 1-16, middle region residues 17-36, and the C-terminal region residues 58-77, whereas the anti-C-terminal antibodies showed the best protective effect in experimental sepsis in rats (Huber-Lang, Sarma et al. 2001, FABSEB J 15(3): 568-70).

Furthermore, a monoclonal antibody against the C-terminal neoepitope of porcine C5a (position 57-74) has been described which neutralized the bioactivity of porcine C5a (Hopken, Mohr et al. 1996, Eur J Immunol 26 (5): 1103-9). The central role of complement in the pathophysiology of major diseases makes it an interesting target for the pharmaceutical industry. Numerous approaches for the clinical substitution, inhibition or modulation of complement have been developed. However, the only complement-specific drug approved by the FDA so far is SOLIRIS® (Eculizumab) for the indication of paroxysmal nocturnal hemoglobinuria (PNH). This monoclonal antibody targets the complement protein C5 preventing the generation of the cleavage products C5a and C5b.

Other monoclonal antibodies, which bind to C5 and block the separation into C5a and C5b, have been generated and suggested for use in therapy of diseases involving tissue damage deriving from uncontrolled activation of the complement system (WO 95/29697, WO 2004/022096, US 2006/0115676, EP 1 878 441). An antibody which binds to C5 and C5a, but does not prevent the activation of C5b, is antibody MAb137-26 (U.S. Pat. No. 7,432,356). Antibodies, specifically binding the cleavage product C5a, have been investigated for treatment of adult respiratory distress syndrome (ARDS) (WO 86/05692) and injurious intravascular complement activation (EP 0 245 993). Moreover, the use of a monoclonal antibody that is reactive to C5a receptor (C5aR) and thereby presumably reduces or inhibits the binding of C5a with C5aR has been proposed in treating immunopathological disorders (WO 2003/062278, NZ 538384, JP 8109200). The use as a therapeutic and diagnostic agent of a humanized anti-C5aR antibody, which binds the human C5a receptor, has recently been published (WO 2009/103113).

Passive immunization strategies using monoclonal antibodies face different limitations, including high costs for antibody production and the development of neutralizing immune responses against the therapeutic antibodies (anti drug antibodies) upon repeated antibody application.

Application of therapeutic antibodies preventing the cleavage of C5 into C5a and C5b might lead to recurrent infections since the production of the C5b fragment (the seed component for the MAC) that is important to lyse bacteria is prevented. Moreover, immunotherapeutic strategies targeting an epitope accessible on C5 and C5a, but not preventing the cleavage of the C5 molecule, are disadvantageous as the active drug compounds (monoclonal antibodies) or the induced target specific antibodies do not distinguish between active and inactive form of C5. Very high antibody concentrations in the serum will be necessary to ensure that a major part of active C5a will be neutralized. The normal C5 protein concentration in the serum is about 75 μg/ml whereas C5a acts at concentrations of 10 to 100 ng/ml.

It is an object of the present invention to provide means and methods for the treatment of complement component C5a induced diseases.

The present invention relates to a vaccine comprising at least one peptide consisting of amino acid sequence LRANISHKDMQLGR (SEQ ID No. 1) or a peptide fragment thereof coupled or fused to a carrier protein comprising at least one T cell epitope, wherein said peptide fragment comprises at least 7 amino acid residues and the amino acid sequence KDMQLGR (SEQ ID No: 7) or KDMQLG (SEQ ID No: 23) under the provision that the peptide fragment does not consist of amino acid sequences HKDMQLGR (SEQ ID No: 16) and HKDMQLG (SEQ ID No: 22).

It turned out that peptide LRANISHKDMQLGR (SEQ ID No. 1), which corresponds to amino acid residues 61 to 74 of human C5a, or a fragment of said peptide is able to induce the in vivo formation of C5a specific antibodies in a mammal, in particular in a human individual. The peptide fragment of SEQ ID No. 1 comprises at least 7, at least 8, at least 9, at least 10, at least 11, at least 12, or at least 13 amino acid residues. Furthermore, fragments of said sequence having a histidine residue at the N-terminus, e.g. HKDMQLGR (SEQ ID No: 16) and HKDMQLG (SEQ ID No: 22), are not part of the invention. According to a preferred embodiment of the present invention the peptide fragment of the vaccine of the present invention comprises a maximum of 13, 12, 11, 10, 9 or 8 amino acid residues.

The vaccine according to the present invention, which may comprise (at least) one, (at least) two, (at least) three or even (at least) four of the above mentioned peptides, allows the active immunization of a mammal, in particular a human individual, where neutralizing antibodies to the complement protein human C5a are induced by vaccination with C-terminal C5a derived fragments when coupled or fused to a peptide or polypeptide or a carrier protein (as a T cell epitope comprising molecule). The peptide/carrier combination is important since peptides of the present invention do not have the capacity to induce relevant amounts of antibodies when injected without coupling to a carrier. Thus, the present invention of an active immunization against hC5a offers advantages over employing monoclonal antibodies therapy for treating C5a-based diseases. Shortcomings of monoclonal C5a antibody therapy including the need for repeated infusions of large amounts of antibody, frequent hospital visits of the patients, and high production cost of humanized antibodies can therefore be circumvented.

In WO 2006/134125 an active immunization against hC5a by the use of a 20-mer C-terminal hC5a fragment (hC5a position 55-74, identified herein as SEQ ID No: 14) linked to virus-like particle (VLP) is disclosed. The compounds of the present invention (Table 1), however, provide C-terminal hC5a-derived peptides which are able to induce a clearly higher immune response against the human C5a when compared to SEQ ID No: 14 (Table 2) (see FIGS. 2 and 3). Moreover, the compounds of the present invention induce antibodies that show higher functional activity in a cell-based assay as well as in an in vivo model when compared to SEQ ID No: 14 (Table 1) (see FIGS. 4, 5, and 6).

The immunization of a mammal with a compound according to the present invention comprising amino acid sequence KDMQLGR (SEQ ID No: 7) results in a much higher immune response than the immunization with the above mentioned 20-mer C-terminal hC5a fragment. Moreover, the immunization of a mammal with the N-terminal part of said 20-mer consisting of amino acid sequence CVVASQLRAN (SEQ ID No: 24) did surprisingly not result in the in vivo formation of C5a specific antibodies (see FIG. 1). This clearly shows that not all fragments of the 20-mer C-terminal hC5a fragment are able to induce C5a specific antibodies.

Hence, vaccination with the C-terminal hC5a derived fragments ranging from 14 to 7 amino acid residues as presented in Table 1 alleviates complement-mediated disorders such as acute or chronic inflammatory diseases, in which C5a plays a crucial role. Due to the specific binding of the peptide-induced antibodies to C5a C-terminal epitopes, C5a molecules will be neutralized within the mammal and the binding of C5a to its receptor (C5aR) will be blocked.

Moreover, this approach does not interfere with the generation and function of the C5b fragment, which plays a major role in host defense, because the induced antibodies do not recognize the entire C5 protein, but only the neoepitope on the cleavage product C5a.

It has been shown that the C-terminal 6-8 residues of C5a alone have the capacity to bind the C5a receptor and more importantly to act as agonist. In addition, a number of high-affinity C-terminal analogues of C5a anaphylatoxin have been published which exhibit an antagonistic effect to the C5a receptor (U.S. Pat. No. 6,821,950; U.S. Pat. No. 6,465,614; U.S. Pat. No. 5,807,824; US 2009/0117171). In contrast to these approaches, where peptides alone (without other components) have been applied to block or activate the C5aR by themselves, in the present invention peptides are coupled to a carrier protein (or to a peptide containing a T cell epitope) before administration in order to induce the formation of specific antibodies against the complement protein C5a.

The compounds/peptides of the present invention are composed of 14 to 7 amino acid residues either with or without arginine at the last position (Table 1: SEQ ID No. 1-13). Peptides with the amino acid residue histidine at the N-terminus were excluded from the sequences to be claimed, because these peptides (SEQ ID No: 16 and SEQ ID No: 22) did not induce functionally active antibodies against hC5a (see FIGS. 4 and 5). The minimal length of the peptide to induce a specific immune response and/or functionally active antibodies against C5a is 7 amino acid residues (FIGS. 2, 3, 4, and 5).

The compound/peptide of the present invention can be synthetically produced by chemical synthesis methods which are well known in the art, either as an isolated peptide or as a part of another peptide or polypeptide. Alternatively, the compound/peptide can be produced in a microorganism such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus which produces the compound/peptide which is then isolated and if desired, further purified. Suitable bacteria for producing the compound/peptide include *E. coli, B. subtilis*, or any other bacterium that is capable of expressing peptides. Suitable yeast types for expressing said compound/peptide include *Saccharomyces cerevisiae, Schizosaccharomyces pombe, Candida* spp., *Pichia pastoris*, or any other yeast capable of expressing peptides. Corresponding methods are well known in the art. Methods for isolating and purifying recombinantly produced peptides are also well known in the art and include e.g. as gel filtration, affinity chromatography, ion exchange chromatography etc.

To facilitate isolation of the compound/peptide, a fusion polypeptide may be generated wherein the compound/peptide is translationally fused (covalently linked) to a heterologous polypeptide which enables isolation by affinity chromatography. Typical heterologous polypeptides are His-Tag (e.g. His6; 6 histidine residues), GST-Tag (Glutathione-S-transferase) etc. The fusion polypeptide facilitates not only the purification of the compound/peptide but may also prevent the degradation of said compound/peptide during purification. If it is desired to remove the heterologous polypeptide after purification, the fusion polypeptide may comprise a cleavage site at the junction between the compound/peptide and the heterologous polypeptide. The cleavage site consists of an amino acid sequence that is cleaved with an enzyme specific for the amino acid sequence at the site (e.g. proteases).

According to a preferred embodiment of the present invention the peptide fragment is selected from the group consisting of RANISHKDMQLGR (SEQ ID No. 2), ANISHKDMQLGR (SEQ ID No. 3), NISHKDMQLGR (SEQ ID No. 4), ISHKDMQLGR (SEQ ID No. 5), SHKDMQLGR (SEQ ID No. 6), KDMQLGR (SEQ ID No. 7), LRANISHKDMQLG (SEQ ID No. 8), RANISHKDMQLG (SEQ ID No. 9), ANISHKDMQLG (SEQ ID No. 10), NISHKDMQLG (SEQ ID No. 11), ISHKDMQLG (SEQ ID No. 12) and SHKDMQLG (SEQ ID No. 13).

According to a further preferred embodiment of the present invention the peptide fragment of LRANISHKDMQLGR (SEQ ID No. 1) comprising KDMQLGR (SEQ ID No. 7) is selected from the group consisting of ANISHKDMQLGR (SEQ ID No. 3), RANISHKDMQLGR (SEQ ID No. 2), NISHKDMQLGR (SEQ ID No. 4), ISHKDMQLGR (SEQ ID No. 5), SHKDMQLGR (SEQ ID No. 6), KDMQLGR (SEQ ID No. 7).

According to a particularly preferred embodiment at least one peptide consisting of amino acid sequence LRANISHKDMQLGR (SEQ ID No. 1) or a peptide fragment thereof comprises at its N- and/or C-terminus at least one cysteine residue bound directly or via a spacer sequence thereto.

This cysteine residue may serve as a reactive group in order to bind the peptide to another molecule or a carrier. For instance, this group may be used to bind the peptide to a carrier protein. The cysteine residue can be bound directly to the peptides of the present invention or via a spacer sequence. The spacer sequence comprises preferably at least one, preferably at least two, more preferably at least three, even more preferably at least four, and optionally a maximum of ten, preferably a minimum of five small non-polar amino acid residues such as glycines.

According to a preferred embodiment of the present invention the carrier is selected from the group consisting of keyhole limpet haemocyanin (KLH), tetanus toxoid (TT), diphtheria toxin (DT), or any other protein or peptide containing T cell epitopes.

According to the present invention the peptide is coupled or fused to a pharmaceutically acceptable carrier, preferably KLH (Keyhole Limpet Haemocyanin), tetanus toxoid, albumin-binding protein, bovine serum albumin, a dendrimer (MAP; Biol. Chem. 358: 581), peptide linkers (or flanking regions) as well as the adjuvant substances described in Singh et al. (Singh et al. 1999, Nat. Biotech. 17: 1075-1081 (in particular those in Table 1 of that document)), and O'Hagan et al. (O'Hagan and Valiante, 2003, Nature Reviews, Drug Discovery 2 (9): 727-735 (in particular the endogenous immuno-potentiating compounds and delivery systems described therein)), or mixtures thereof. The conjugation chemistry (e.g. via heterobifunctional compounds such as GMBS and of course also others as described in "Bioconjugate Techniques", Greg T. Hermanson) in this context can be selected from reactions known to the skilled man in the art. Moreover, the vaccine composition may be formulated with an adjuvant, preferably a low soluble aluminum composition, in particular aluminum hydroxide. Of course, also adjuvants like MF59, aluminum phosphate, calcium phosphate, cytokines (e.g. IL-2, IL-12, GM-CSF), saponins (e.g. QS21), MDP derivatives, CpG oligos, LPS, MPL, polyphosphazenes, emulsions (e.g. Freund's, SAF), liposomes, virosomes, iscoms, cochleates, PLG microparticles, poloxamer particles, virus-like particles, heat-labile enterotoxin (LT), cholera toxin (CT), mutant toxins (e.g. LTK63 and LTR72), microparticles and/or polymerized liposomes may be used.

According to a preferred embodiment of the present invention the peptide is formulated with an adjuvant, preferably adsorbed to alum.

The vaccine of the present invention may be administered subcutaneously, intramuscularly, intradermally, intravenously (see e.g. "Handbook of Pharmaceutical Manufacturing Formulations", Sarfaraz Niazi, CRC Press Inc, 2004). Depending on the route of administration, the medicament may comprise respective carriers, adjuvants, and/or excipients.

The vaccine according to the present invention contains the compound according to the invention in an amount of 0.1 ng to 10 mg, preferably 10 ng to 1 mg, in particular 100 ng to 100 μg, or, alternatively, e.g. 100 fmol to 10 μmol, preferably 10 pmol to 1 μmol, in particular 100 pmol to 100 nmol. The compound or peptide of the present invention is administered to a mammal in an amount of preferably 100 ng to 1 mg, more preferably 1 μg to 500 μg, even more preferably 10 μg to 100 μg, in particular 20 to 40 or 30 μg, per doses. Typically, the vaccine may also contain auxiliary substances, e.g. buffers, stabilizers etc. The vaccine according to the present invention is applied 3 to 6 times in a time interval of two weeks up to 2 month. Upon existing anti C5a antibodies the vaccine is applied in regular intervals of approximately 6 month.

According to a preferred embodiment of the present invention the vaccine is used in the treatment of a complement-mediated disorder. Thus the present invention relates also to a method for treating an individual suffering from a complement-mediated disorder by administering a vaccine according to the present invention.

The complement-mediated disorder is preferably an inflammatory disease, preferably a chronic inflammatory disease.

The inflammatory disease is preferably selected from the group consisting of age-related macular degeneration (AMD), a neurodegenerative disorder, preferably Alzheimer's disease, Parkinson's disease or Huntington's disease, allergic asthma, atherosclerosis, Guillain-Barre syndrome, vasculitis, inflammatory dermatitis, preferably psoriasis and urticaria, rheumatoid arthritis, antiphospholipid syndrome (APS), multiple sclerosis, hemolytic uremic syndrome, and systemic lupus erythematosus (SLE).

The complement-mediated disorder is preferably ischemia-reperfusion injury, acute lung injury, acute respiratory distress syndrome (ARDS), sepsis, cancer, pregnancy complications such as preeclampsia, recurrent spontaneous abortions, intra-uterine growth retardation and APS.

A complement-mediated disorder—according to the present invention—is also a disorder which involves undesirable or inappropriate complement activity such as hemodialysis-associated thrombosis. This activity can be determined by methods known in the art. The disorders which can be treated with the vaccine according to the present invention are characterized by an increased C5a activity.

AMD is a medical condition which usually affects older adults and results in a loss of vision in the center of the visual field (the macula) because of damage to the retina. It occurs in "dry" and "wet" forms, whereas the dry form accounts for 90% of all AMD instances. One of the earliest clinical hallmarks of wet and dry AMD is the appearance of amorphous lipoproteinaceous deposits accumulating extra-cellularly in areas close to the retinal pigment epithelium. These pathogenic components are called drusen. Recent studies have implicated local inflammation and activation of the complement cascade in the formation of drusen, the hallmark of dry AMD. This is in line with other studies showing that beside other molecules the complement component C5, accumulates within these drusen.

Moreover, it has been shown that C5a, besides VEGF (C5a is involved in the release of VEGF), plays a key role in the induction of the choroidal neovascularization, which takes place in the wet form of AMD. Most importantly, the neutralizing antibodies against C5a could be shown to be able to stop the progression of the disease in animal models.

Taken together, there is strong support for complement-mediated disease in wet and dry forms of AMD and thus, C5a appears to be an optimal target for the treatment of both forms of AMD.

Complement-mediated inflammation, predominately caused by C5a, is proposed to play a role in the acceleration or progression of Alzheimer's disease. Prolonged complement activation is triggered by fibrillar Aβ plaques in Alzheimer's disease brain and many manifestations of the disease can be contributed to C5a-recruited and activated glia that promote inflammatory events. Similar events may apply to Parkinson's disease and Huntington's disease. Furthermore, preliminary data indicate a specific pathogenic role for the activation fragment of complement C5 (C5a) in motor neuron disease, a group of degenerative disorders causing progressive motor neuron death leading to eventual paralysis and death.

Blockage of C5aR clearly reduces airway inflammation and airway hyper-responsiveness in experimental allergic asthma. However, the role of complement component C5 in asthma remains controversial. C5 has been described as either promoting or protecting against airway hyper-responsiveness in experimental allergic asthma, suggesting a dual role for C5a in allergic asthma. One hypothesis is that C5aR signaling during allergen sensitization protects from the development of pulmonary allergy but enhances the allergic phenotype in an inflamed pulmonary environment during the effector phase. Thus, C5aR blockage might be of therapeutic benefit for the treatment of established asthma.

C5a plays also a role in atherosclerosis. C3a and C5a are expressed in human coronary plaques. Moreover, it has recently been shown that C5a predicts cardiovascular events in patients with advanced atherosclerosis and that elevated serum levels of C5a are associated with the development of restenosis after balloon angioplasty of the superficial femoral artery.

Vasculitis is an inflammatory process of blood vessels, histopathologically characterized by inflammation and fibrinoid necrosis of the vessel wall. The clinical spectrum of this form of vasculitis is variable ranging from purpura to severe proliferative glomerulonephritis and the complement systems is supposed to be critically involved in these processes. For instance, C5a plays an important role in anti-neutrophil cytoplasmic autoantibody (ANCA)-associated vasculitis, a relatively uncommon but potentially life-threatening systemic autoimmune disease. ANCA-induced necrotizing crescentic glomerulonephritis requires complement participation in its pathogenesis. C5a and the neutrophil C5aR may compose an amplification loop for ANCA-mediated neutrophil activation. The C5aR may provide a new therapeutic target for ANCA-induced necrotizing crescentic glomerulonephritis.

Complement activation is involved in the pathogenesis of the inflammatory changes in autoimmune dermatitis including bullous pemphigoid (BP), psoriasis vulgaris, and chronic urticaria. In pemphigus complement activation by pemphigus antibody in the epidermis seems to be responsible for the development of characteristic inflammatory changes termed eosinophilic spongiosis. In psoriatic scales high levels of C5a are found, indicating that complement activation is involved in this disease. Psoriasis is known to be a T cell mediated disease, however, neutrophils and mast cells may also be involved in the pathogenesis of the disease. T cells and neutrophils are chemo-attracted by C5a, therefore C5a could be an important therapeutic target for treatment of psoriasis.

Complement activation also contributes to the autoimmune inflammatory disease, rheumatoid arthritis. It appears that anaphylatoxin C5a is the main product of complement activation responsible for tissue damage in rheumatoid arthritis although deposition of membrane attack complex as well as opsonization with fragments of C3b are also important.

The role of complement in the pathogenesis of systemic lupus erythematosus (SLE) remains controversial. On the one hand, complement components appear to mediate autoantibody-initiated tissue damage. On the other hand, the complement system appears to have protective features as hereditary deficiencies of some complements are associated with an increase risk for SLE. It is known that patients with SLE often have hypocomplementemia. Moreover, it was demonstrated that C5a/C5aR signaling plays an important role in the pathogenesis of central nervous system lupus by regulating the integrity of the blood-brain barrier. The potential of C5a/C5aR blockage was highlighted as a promising therapeutic strategy in SLE.

It appears that the tissue reperfusion (R) and not the ischemia (I) activates complement and leads to inflammation-induced damage. Even though exact involvement of complement activation in I/R injury is still unclear, several experimental studies have indicated a connection between complement and the pathogenesis of I/R injury, and have suggested complement inhibition as a potent therapy. For instance, in a murine myocardial I/R injury model a systemic C5 inhibition, 30 minutes prior to reperfusion, significantly protected mice from myocardial I/R injury.

Complement activation has been demonstrated in many forms of acute lung injury. C5a concentration is increased in broncho-alveolar lavage fluids (BALF) in acute lung injury induced by acid instillation, and C5a concentration is also elevated in transplanted lungs in human. C5a attracts neutrophils into the lung, and directly actives neutrophils, macrophages, and endothelial cells. The protective role of anti-C5a was associated with drastic reduction in BALF levels of TNF-α, as well as a profound decrease in lung vascular intercellular adhesion molecule ICAM-1 expression, suggesting that C5a is essential in the foundation of the inflammatory network, regulating the expression of inflammatory mediators and expression of adhesion molecules.

Acute lung injury and acute respiratory distress syndrome (ARDS) is characterized by the presence of fibrin-rich inflammatory exudates in the intra-alveolar spaces and the extensive migration of neutrophils into alveoli of the lungs. Pharmacological blockade of TNF-α and C5a signaling in neutrophils from healthy volunteers was able to significantly diminish the BALF induced procoagulant activity of these otherwise normal cells and cause a concomitant loss of tissue factor (TF) expression. These results indicate that C5a and TNF-α signaling contributes to the induction of TF expression in neutrophils accumulating in the alveoli of lungs affected by ARDS.

During the onset of sepsis, the inflammatory system becomes hyperactive, involving both cellular and humoral defense mechanism. It has been shown that complement activation during human sepsis, especially as reflected in elevated levels of C5a, is associated with significantly reduced survival rates together with multi-organ failure when compared with less severe septic patients and survivors. Moreover, interception of either C5a or C5aR dramatically improves survival during experimental sepsis in rodents. Thus, C5a seems to be a key player for the development of sepsis and interference of C5a/C5aR binding may present a potent clinical approach for preventive treatment of patients at high risk for developing sepsis.

In cardiopulmonary bypass and hemodialysis, C5a is generated as a result of activation of the alternative complement pathway when human blood makes contact with the artificial surface of the heart-lung machine or kidney dialysis machine. C5a causes increased capillary permeability and edema, broncho-constriction, pulmonary vasoconstriction, leukocyte and platelet activation and infiltration to tissues, in particular the lung. Administration of an anti-C5a monoclonal antibody was shown to reduce cardiopulmonary bypass and cardioplegia-induced coronary endothelial dysfunction.

Tumor-driven complement activation can provide tumor growth advantage. The generation of complement C5a in a tumor microenvironment enhances tumor growth by suppressing the antitumor $CD8^+$ T cell mediated response. Using a mouse model of tumor growth revealed that deficiency or blockage of C5aR is associated with retardation of tumor growth. Complement inhibition is therefore considered as an effective and promising approach in anticancer therapy.

A significant increase of complement activation was associated with different pathologic pregnancy outcomes, namely preeclampsia, recurrent spontaneous abortions, intra-uterine growth retardation, and antiphospholipid syndrome (APS). Women with preeclampsia showed increased plasma concentration of C5a compared to normal pregnant women. Concerning APS, antiphospholipid antibodies and complement activation (via C3a, C5a, and MAC) may cooperate in triggering a local inflammatory process, eventually leading to placental thrombosis, hypoxia, and neutrophil infiltration. Tissue factor (TF) represents the link between C5a and neutrophil activation in antiphospholipid antibody induced fetal injury.

Summarizing the peptide-induced immune response against C5a results in an effective therapy for C5a mediated (chronic inflammatory) diseases including neurodegenerative diseases such as Alzheimer's disease (see e.g. Fonseca, M. I. et al. (2009), J Immunol "Treatment with a C5aR Antagonist Decreases Pathology and Enhances Behavioral Performance in Murine Models of Alzheimer's Disease." and Klos, A. et al. (2009), Mol Immunol "The role of the anaphylatoxins in health and disease."), Parkinson's disease (see e.g. McGeer, P. L. et al. (2004), Parkinsonism Relat Disord "Inflammation and neurodegeneration in Parkinson's disease."), Huntington's disease (see e.g. Singhrao, S. K. et al. (1999), Exp Neurol "Increased complement biosynthesis by microglia and complement activation on neurons in Huntington's disease.") and age-related macula degeneration (see e.g. Nozaki, M. et al. (2006), Proc Natl Acad Sci "Drusen complement components C3a and C5a promote choroidal neovascularization."), rheumatoid arthritis (see e.g. Okroj, M. et al. (2007), Ann Med "Rheumatoid arthritis and the complement system."), systemic lupus erythematosus (SLE) (see e.g. Chen, M. et al. (2009), J Autoimmun "The complement system in systemic autoimmune disease."; Jacob, A. et al. (2010), J Neuroimmunol "Inhibition of C5a receptor alleviates experimental CNS lupus." and Jacob, A, et al. (2010), FASEB J "C5a alters blood-brain barrier integrity in experimental lupus."), asthma (see e.g. Kohl, J. et al. (2006), J Clin Invest "A regulatory role for the C5a anaphylatoxin in type 2 immunity in asthma."), vasculitis, antiphospholipid syndrome (APS), atherosclerosis, inflammatory dermatitis such as psoriasis and chronic urticaria, Guillain-Barre syndrome, hemolytic uremic syndrome, and multiple sclerosis. Since uncontrolled hC5a release contributes to other pathological conditions such as ischemia and reperfusion injury, sepsis, acute lung injury, complications associated with hemodialysis, cancer, pregnancy complication such as preeclamsia and APS, neutralization of C5a by active immunization may provide an effective therapy for these pathological complications as well.

A further aspect of the present invention relates to a vaccine comprising LRANISHKDMQLGR (SEQ ID No. 1) or a peptide fragment thereof coupled or fused to a carrier protein comprising at least one T cell epitope, wherein said peptide fragment comprises at least 7 amino acid the amino acid sequence KDMQLGR (SEQ ID No: 7) or KDMQLG (SEQ ID No: 23) under the provision that the peptide fragment does not consist of amino acid sequences HKDMQLGR (SEQ ID No: 16).

Another aspect of the present invention relates to a peptide having an amino acid sequence selected from the group of LRANISHKDMQCGR (SEQ ID No: 1), RANISHKDMQLGR (SEQ ID No. 2), ANISHKDMQLGR (SEQ ID No. 3), NISHKDMQLGR (SEQ ID No. 4), ISHKDMQLGR (SEQ ID No. 5), SHKDMQLGR (SEQ ID No. 6), KDMQLGR (SEQ ID No. 7), LRANISHKDMQLG (SEQ ID No. 8), RANISHKDMQLG (SEQ ID No. 9), ANISHKDMQLG (SEQ ID No. 10), NISHKDMQLG (SEQ ID No. 11), ISHKDMQLG (SEQ ID No. 12) and SHKDMQLG (SEQ ID No. 13).

The present invention is further illustrated in the following figures and examples, however, without being restricted thereto.

EXAMPLES

The object of the present invention is to develop a neutralizing active immune response against excessive human C5a in order to avert its pathological activity. In the approach described the C-terminal neoepitope, which becomes accessible upon cleavage of C5 protein by the C5 convertase, is targeted. Thus by vaccination, the role of C5b in host defense will be maintained, whereas the excessive activity of the anaphylatoxin C5a is supposed to be blocked.

Material and Methods:

Immunization of Mice

Female BALB/c mice (6-8 weeks) were primed and boost-immunized four times in biweekly intervals with KLH-conjugated peptide vaccines (200 µl subcutaneously in phosphate buffer pH 7.4). Aluminum hydroxide was used as an adjuvant. Five to six mice were used for injection with the respective KLH-conjugated peptide vaccine. Experiments were repeated and representatives thereof are shown below.

Antibody titers of the mouse sera were analyzed by the Enzyme Linked Immunosorbent Assay (ELISA). Titers were calculated as the sera dilution giving half-maximal binding (i.e. $OD_{max}/2$) and the median titers of 5 to 6 mice per group are presented. The functional activity of the induced antibodies was assessed by the glucuronidase enzyme release assay.

Example 1

Immunogenicity Testing of the Previously Described 20 Amino Acid Long Immunogenic C-Terminal Fragment of hC5a, the N— and the C-Terminal Part Thereof In this example the 20 amino acid long C-terminal fragment of human C5a (SEQ ID No: 14) as well as the N-terminal (SEQ ID No: 24) and the C-terminal part (SEQ ID No: 7) thereof were tested for their immunogenicity. Mice were immunized with the indicated peptides and the median titers of the induced antibodies against hC5a are shown in FIG. 1.

Figure 1:
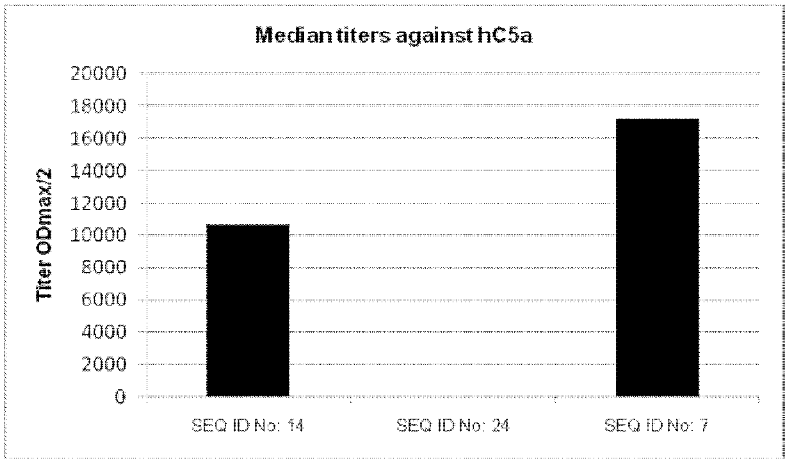
FIG. 1 shows immunogenicity testing of the previously described 20 amino acid long immunogenic C-terminal fragment of hC5a (SEQ ID No: 14), the N- and the C-terminal part thereof (SEQ ID No: 7 and 24).

The hC5a fragment position 55-74 (SEQ ID No: 14) as well as the C-terminal part thereof (SEQ ID No: 7) were able to induce titers against hC5a, but not the N-terminal part thereof (SEQ ID No: 24) (FIG. 1). Thus, the C-terminal part (SEQ ID No: 7) of the 20 mer peptide is crucial for the induction of a humoral immune response to hC5a, whereas the N-terminal fragment (SEQ ID No: 24) is negligible.

Example 2

Immune Response to hC5a Induced by Peptides Covering 20 to 4 Amino Acids of the C-Terminus of hC5a (SEQ ID No: 1-7 and SEQ ID No: 14-19)

Thirteen C-terminal hC5a derived peptides varying from 20 to 4 amino acids residues (SEQ ID No: 1-7 and SEQ ID No: 14-19 as indicated in Table 2) where tested for their ability to induce a humoral immune response against hC5a.

Figure 2:
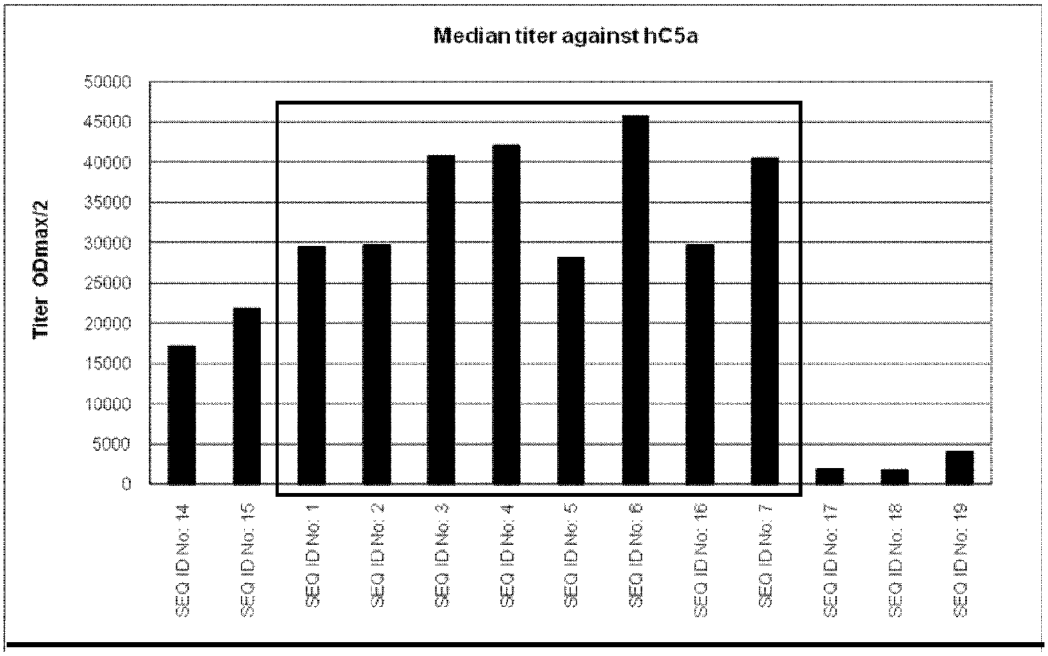
FIG. 2 shows the immune response to hC5a induced by peptides covering 20 to 4 amino acids of the C-terminus of hC5a (SEQ ID No: 1-7 and SEQ ID No: 14-19).

Mice were immunized with the indicated peptides and the median titers of the induced antibodies against hC5a are shown in FIG. 2. Although all tested C-terminal peptides were able to induce antibodies which bind to the injected peptide (data not shown), only 7 peptides induced high titers against the protein hC5a as shown in FIG. 2 (boxed). C-terminal peptides shorter than 7 amino acids (SEQ ID No: 17-19) do not induce a relevant humoral immune response to hC5a (FIG. 2). In all instances an immune response against the un-cleaved C5 protein was not observed (data not shown).

Example 3

Immune Response to hC5a Induced by Peptides Covering 19 to 5 Amino Acids of the C-Terminus of hC5a without Arginine at the Last Position (SEQ ID No: 8-13 and SEQ ID No: 20-23)

Figure 3:
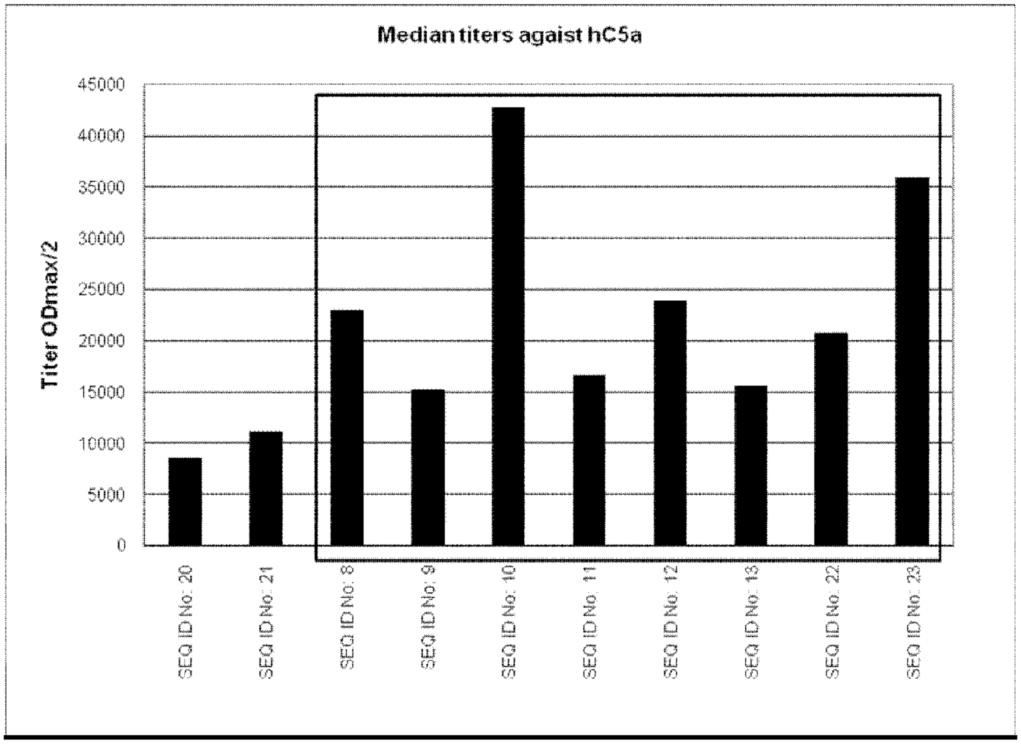
FIG. 3 shows the immune response to hC5a induced by peptides covering 19 to 6 amino acids of the C-terminal hC5a fragment without arginine at the position 74 (SEQ ID No: 8-13 and SEQ ID No: 20-23).

Ten C-terminal hC5a derived peptides without the arginine at the last position (SEQ IC No: 8-13 and SEQ ID No:

20-23 as indicated in Table 2) were used to raise antibodies against hC5a. Mice were immunized with the indicated peptides and the median titers of the induced antibodies against hC5a are shown in FIG. 3. All peptides tested were able to induce antibodies which bind to the injected peptide (data not shown), but only the SEQ ID No: 8-13 and SEQ ID No: 22-23 showed a high response to hC5a (FIG. 3, boxed). An immune response to the un-cleaved C5 protein was not observed (data not shown).

Example 4

Assessment of the Functional Activity of the Antibodies Induced by Immunization with C-Terminal Peptides with Arginine (SEQ ID No: 1-7 and SEQ ID No: 14-17) and without Arginine at the Last Position (SEQ ID No: 8-13 and SEQ ID No: 20-23)

The inhibitory activity of peptide-induced antibodies against hC5a was tested by the glucuronidase enzyme release assay. β-glucuronidase is released from differentiated human U937 cells upon stimulation with hC5a. This effect can be blocked by the addition of peptide induced anti-hC5a immune sera which is shown in FIGS. 4 and 5.

Briefly, U937 cells were differentiated for 5 days with 0.5 mM cyclic adenosine 3':5'-monophorphate (cAMP) in RPMI, 10% FCS. On day 5 the cells were pre-treated with cytochalasin B (2.5 μg/ml) for 10 minutes at 37° C. For each approach $1.8\times10^5$ pre-treated cells were stimulated either with 25 nM hC5a alone or with 25 nM hC5a and 4% serum derived from mice immunized with different peptides (SEQ ID No: 1-17 and SEQ ID No: 20-23 as indicated in Table 2) in a final volume of 120 μl HAG-CM buffer (20 mM HEPES pH=7.4, 125 mM NaCl, 5 mM KCl, 0.5 mM glucose, 1 mM $CaCl_2$, 1 mM $MgCl_2$, 0.25% BSA). After the incubation for 10 minutes at 37° C. the cells were pelleted, the supernatant was transferred to a 96-well microtiter plate, and diluted 1:1 with 0.01 M P-nitrophenyl-β-D-glucuronide (dissolved in 0.1 M sodium acetate pH=4.0) in a total volume of 150 μl. The microtiter plate was incubated for 1 h at 37° C. in the dark. Then the reaction was stopped by the addition of 0.4 M glycine buffer (pH=10.0). β-glucuronidase converts P-nitrophenyl-β-D-glucuronide to a yellowish color that is read out at 405 nm.

Figure 4:
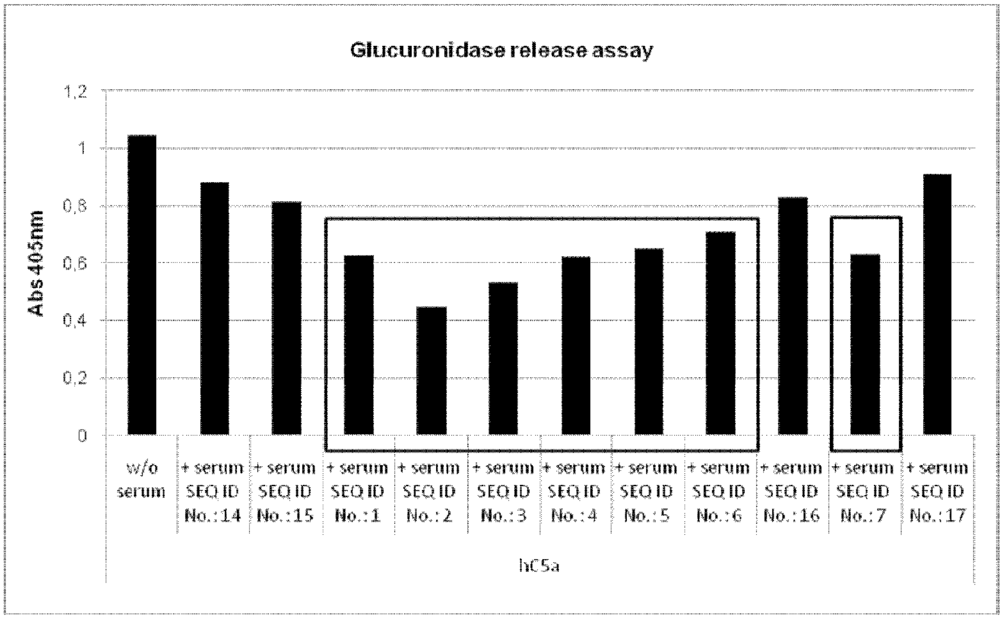
FIG. 4 shows the assessment of the functional activity of the antibodies induced by immunization with SEQ ID No: 1-7 and SEQ ID No: 14-17.
Figure 5:
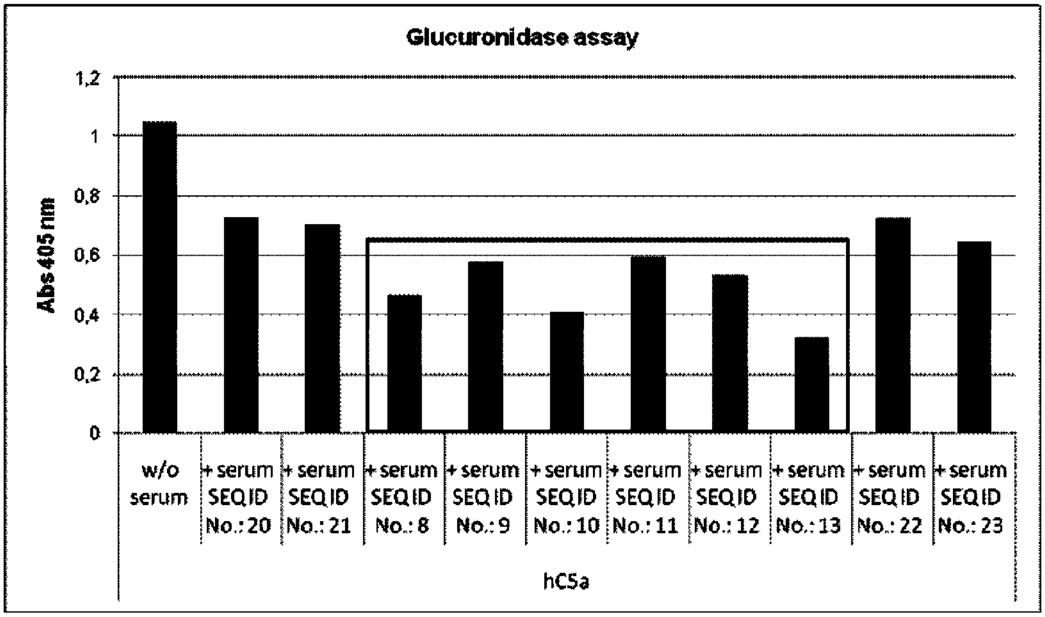
FIG. 5 shows the assessment of the functional activity of the antibodies induced by the immunization with SEQ ID No: 8-13 and SEQ ID No: 20-23.

In FIGS. 4 and 5 the glucuronidase release (indicated as the absorption at 405 nm) of hC5a stimulated cells with and without the addition of peptide-induced immune sera (pools of 6 to 5 animals) is shown. Immune sera with the best inhibitory activity, SEQ ID No: 1-7, and SEQ ID No: 8-13 are encompassed by the present invention (FIGS. 4 and 5, boxed).

In general, a good correlation of the titer and the functional activity of the peptide-induced sera was observed (FIGS. 2, 3, 4, and 5). However, the immune sera of the SEQ ID No: 16, 22, and 23 were able to induce good titers against hC5a (FIGS. 2 and 3), but showed only limited functional activity in the glucuronidase assay (FIGS. 4 and 5). These peptides which had either a histidine residue at the N-terminus or were shorter than 7 amino acids residues did not induce functional active antibodies against hC5a and were therefore excluded from the panel of peptides of the present invention.

Example 5

In Vivo Evaluation of the Present Invention, a Peptide-Induced Active Immunization Against hC5a Complement activation is well known for inducing a transient neutropenia/neutrophilia in the animal model. The injection of purified human C5a in rabbits showed an immediate neutropenia, lasting only a few minutes, followed by a significant neutrophilia persisting during a 4-hour period. Circulated neutrophils are activated by C5a and thereby become deformed and adherent, leading to a neutropenia, sequestration, and depletion of cells from circulation. After the neutropenic event an immediate neutrophilic response is required for replacement of this particular cell population and to re-establish homeostasis.

The effect of peptide-induced active immunization against hC5a was tested in the in vivo model of human C5a-induced neutropenia model in rabbits.

Immunization of Rabbits

Male New Zealand White rabbits (6-8 weeks) were primed and boost-immunized four times biweekly by subcutaneous injections (200 μl at the lower back and 200 μl on the thigh) with KLH-conjugated peptide vaccines. Aluminum hydroxide was used as an adjuvant. Four rabbits were used for injection with the respective KLH-conjugated peptide vaccine.

Figure 6:
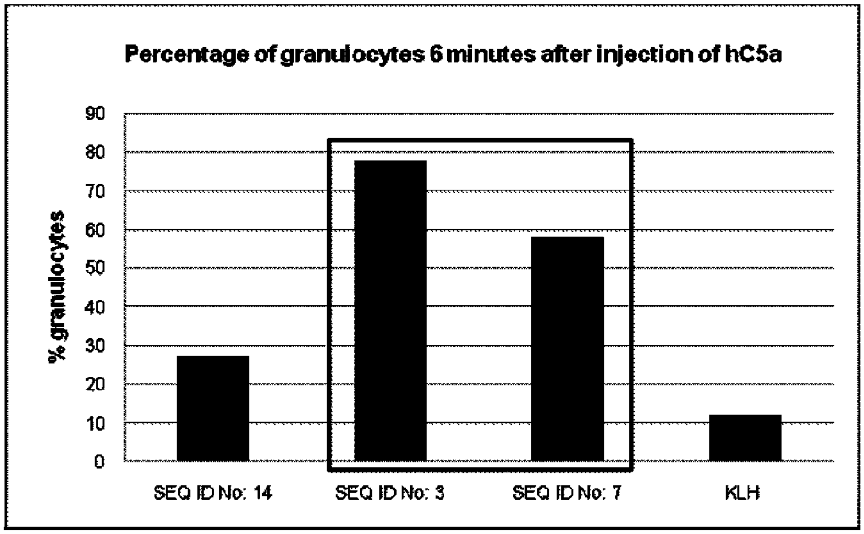
FIG. 6 shows the prevention of human C5a-induced neutropenia in rabbits by immunization with SEQ ID No: 3 and SEQ ID No: 7 of the present invention.

The SEQ ID No: 14 (Table 2); SEQ ID No: 3 and SEQ ID No: 7 both representatives for the hC5a C-terminal derived peptides claimed by the present invention (Table 1); and the carrier protein KLH alone were used for the immunization procedure described above. After the third boost all rabbits were injected with 2 μg/kg hC5a in the marginal vein of the right ear and blood was collected from the central artery of the left ear 6 minutes after the injection. The number of granulocytes was determined and compared to the number of granulocytes of the pre-blood collected two minutes before the injection of hC5a. The median values of each group are presented in FIG. 6.

This example revealed a clear reduction of hC5a-induced neutropenia in rabbits which were immunized with representatives of the compounds of the present invention (SEQ ID No: 3 and SEQ ID No: 7 KLH-conjugated peptide vaccines), but not in rabbits immunized with KLH-conjugated SEQ ID No: 14 vaccine or KLH alone.

TABLE 1

C-terminal fragments of hC5a used in the present invention for an active peptide-induced immune response to hC5a.

| Sequence identification number | Amino acid position of hC5a (>gi\|109731812) | Sequence |
|---|---|---|
| SEQ ID No: 1 | 61-74 | LRANISHKDMQLGR |
| SEQ ID No: 2 | 62-74 | RANISHKDMQLGR |
| SEQ ID No: 3 | 63-74 | ANISHKDMQLGR |

TABLE 1-continued

C-terminal fragments of hC5a used in the present invention for an active peptide-induced immune response to hC5a.

| Sequence identification number | Amino acid position of hC5a (>gi\|109731812) | Sequence |
|---|---|---|
| SEQ ID No: 4 | 64-74 | NISHKDMQLGR |
| SEQ ID No: 5 | 65-74 | ISHKDMQLGR |
| SEQ ID No: 6 | 66-74 | SHKDMQLGR |
| SEQ ID No: 7 | 68-74 | KDMQLGR |
| SEQ ID No: 8 | 61-73 | LRANISHKDMQLG |
| SEQ ID No: 9 | 62-73 | RANISHKDMQLG |
| SEQ ID No: 10 | 63-73 | ANISHKDMQLG |
| SEQ ID No: 11 | 64-73 | NISHKDMQLG |
| SEQ ID No: 12 | 65-73 | ISHKDMQLG |
| SEQ ID No: 13 | 66-73 | SHKDMQLG |

TABLE 2

Peptides used for immunogenicity studies as described in EXAMPLE 1, 2, and 3.

| Sequence identification number | Amino acid position of hC5a (>gi\|109731812) | Sequence |
|---|---|---|
| SEQ ID No: 14 | 55-74 | CVVASQLRANISHKDMQLGR |
| SEQ ID No: 15 | 60-74 | QLRANISHKDMQLGR |
| SEQ ID No: 1 | 61-74 | LRANISHKDMQLGR |
| SEQ ID No: 2 | 62-74 | RANISHKDMQLGR |
| SEQ ID No: 3 | 63-74 | ANISHKDMQLGR |
| SEQ ID No: 4 | 64-74 | NISHKDMQLGR |
| SEQ ID No: 5 | 65-74 | ISHKDMQLGR |
| SEQ ID No: 6 | 66-74 | SHKDMQLGR |
| SEQ ID No: 16 | 67-74 | HKDMQLGR |
| SEQ ID No: 7 | 68-74 | KDMQLGR |
| SEQ ID No: 17 | 69-74 | DMQLGR |
| SEQ ID No: 18 | 70-74 | MQLGR |
| SEQ ID No: 19 | 71-74 | QLGR |
| SEQ ID No: 20 | 55-73 | CVVASQLRANISHKDMQLG |
| SEQ ID No: 21 | 60-73 | QLRANISHKDMQLG |
| SEQ ID No: 8 | 61-73 | LRANISHKDMQLG |
| SEQ ID No: 9 | 62-73 | RANISHKDMQLG |
| SEQ ID No: 10 | 63-73 | ANISHKDMQLG |
| SEQ ID No: 11 | 64-73 | NISHKDMQLG |
| SEQ ID No: 12 | 65-73 | ISHKDMQLG |
| SEQ ID No: 13 | 66-73 | SHKDMQLG |
| SEQ ID No: 22 | 67-73 | HKDMQLG |

TABLE 2-continued

| Peptides used for immunogenicity studies as described in EXAMPLE 1, 2, and 3. | | |
|---|---|---|
| Sequence identification number | Amino acid position of hC5a (>gi\|109731812) | Sequence |
| SEQ ID No: 23 | 68-73 | KDMQLG |
| SEQ ID No: 24 | 55-64 | CVVASQLRAN |

The invention claimed is:

1. A method of inhibiting C5a in a patient in need thereof, the method comprising:

administering to the patient a composition comprising at least one peptide coupled or fused to a carrier protein comprising at least one T cell epitope, wherein said peptide is selected from the group consisting of ANISHKDMQLGR (SEQ ID No. 3), NISHKDMQLGR (SEQ ID No. 4), SHKDMQLGR (SEQ ID No. 6), and KDMQLGR (SEQ ID No. 7), wherein the patient has a disorder involving the complement activation system.

2. The method according to claim 1, wherein the disorder is an inflammatory disease.

3. The method according to claim 2, wherein the inflammatory disease is selected from the group consisting of age-related macular degeneration (AMD), a neurodegenerative disorder, Parkinson's disease, Huntington's disease, asthma, atherosclerosis, vasculitis, dermatitis, hemolytic uremic syndrome, rheumatoid arthritis, Guillain-Barre syndrome, multiple sclerosis, antiphospholipid syndrome, hemolytic uremic syndrome, and systemic lupus erythematosus (SLE).

4. The method according to claim 1, wherein the disorder is selected from the group consisting of ischemia/reperfusion injury, acute lung injury, acute respiratory distress syndrome, sepsis, cancer, a pregnancy complication, recurrent spontaneous abortion, intra-uterine growth retardation, antiphospholipid syndrome, and hemodialysis-associated thrombosis.

5. The method according to claim 1, wherein the composition further comprises alum.

6. The method according to claim 1, wherein the disorder is a chronic inflammatory disease.

7. The method according to claim 1, wherein the at least one peptide comprises at its N-terminus at least one cysteine residue bound directly or via a spacer sequence thereto.

8. The method according to claim 1, wherein the carrier protein is selected from the group consisting of keyhole limpet haemocyanin (KLH), tetanus toxoid (TT) or diphtheria toxin (DT).

9. The method according to claim 1, wherein the disorder is Alzheimer's disease.

10. The method according to claim 1, wherein the disorder is age related macular degeneration (AMD).

11. The method according to claim 1, wherein the disorder is atherosclerosis.

12. The method according to claim 1, wherein the composition comprises ANISHKDMQLGR (SEQ ID No. 3).

13. The method according to claim 1, wherein the composition comprises NISHKDMQLGR (SEQ ID No. 4).

14. The method according to claim 1, wherein the composition comprises SHKDMQLGR (SEQ ID No. 6).

15. The method according to claim 1, wherein the composition comprises KDMQLGR (SEQ ID No. 7).

* * * * *

SEQUENCE LISTING

<160> NUMBER OF SEQ ID NOS: 24

<210> SEQ ID NO 1
<211> LENGTH: 14
<212> TYPE: PRT
<213> ORGANISM: Artificial Sequence
<220> FEATURE:
<223> OTHER INFORMATION: C5a fragment

<400> SEQUENCE: 1

Leu Arg Ala Asn Ile Ser His Lys Asp Met Gln Leu Gly Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: C5a fragment

<400> SEQUENCE: 2

Arg Ala Asn Ile Ser His Lys Asp Met Gln Leu Gly Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: C5a fragment

<400> SEQUENCE: 3

Ala Asn Ile Ser His Lys Asp Met Gln Leu Gly Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: C5a fragment

<400> SEQUENCE: 4

Asn Ile Ser His Lys Asp Met Gln Leu Gly Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: C5a fragment

<400> SEQUENCE: 5

-continued

```
Ile Ser His Lys Asp Met Gln Leu Gly Arg
1               5                   10


<210> SEQ ID NO 6
<211> LENGTH: 9
<212> TYPE: PRT
<213> ORGANISM: Artificial Sequence
<220> FEATURE:
<223> OTHER INFORMATION: C5a fragment

<400> SEQUENCE: 6

Ser His Lys Asp Met Gln Leu Gly Arg
1               5


<210> SEQ ID NO 7
<211> LENGTH: 7
<212> TYPE: PRT
<213> ORGANISM: Artificial Sequence
<220> FEATURE:
<223> OTHER INFORMATION: C5a fragment

<400> SEQUENCE: 7

Lys Asp Met Gln Leu Gly Arg
1               5


<210> SEQ ID NO 8
<211> LENGTH: 13
<212> TYPE: PRT
<213> ORGANISM: Artificial Sequence
<220> FEATURE:
<223> OTHER INFORMATION: C5a fragment

<400> SEQUENCE: 8

Leu Arg Ala Asn Ile Ser His Lys Asp Met Gln Leu Gly
1               5                   10


<210> SEQ ID NO 9
<211> LENGTH: 12
<212> TYPE: PRT
<213> ORGANISM: Artificial Sequence
<220> FEATURE:
<223> OTHER INFORMATION: C5a fragment

<400> SEQUENCE: 9

Arg Ala Asn Ile Ser His Lys Asp Met Gln Leu Gly
1               5                   10


<210> SEQ ID NO 10
<211> LENGTH: 11
<212> TYPE: PRT
<213> ORGANISM: Artificial Sequence
<220> FEATURE:
<223> OTHER INFORMATION: C5a fragment

<400> SEQUENCE: 10

Ala Asn Ile Ser His Lys Asp Met Gln Leu Gly
1               5                   10


<210> SEQ ID NO 11
<211> LENGTH: 10
<212> TYPE: PRT
<213> ORGANISM: Artificial Sequence
<220> FEATURE:
<223> OTHER INFORMATION: C5a fragment

<400> SEQUENCE: 11
```

-continued

```
Asn Ile Ser His Lys Asp Met Gln Leu Gly
1               5                   10


<210> SEQ ID NO 12
<211> LENGTH: 9
<212> TYPE: PRT
<213> ORGANISM: Artificial Sequence
<220> FEATURE:
<223> OTHER INFORMATION: C5a fragment

<400> SEQUENCE: 12

Ile Ser His Lys Asp Met Gln Leu Gly
1               5


<210> SEQ ID NO 13
<211> LENGTH: 8
<212> TYPE: PRT
<213> ORGANISM: Artificial Sequence
<220> FEATURE:
<223> OTHER INFORMATION: C5a fragment

<400> SEQUENCE: 13

Ser His Lys Asp Met Gln Leu Gly
1               5


<210> SEQ ID NO 14
<211> LENGTH: 20
<212> TYPE: PRT
<213> ORGANISM: Artificial Sequence
<220> FEATURE:
<223> OTHER INFORMATION: C5a fragment

<400> SEQUENCE: 14

Cys Val Val Ala Ser Gln Leu Arg Ala Asn Ile Ser His Lys Asp Met
1               5                   10                  15

Gln Leu Gly Arg
            20


<210> SEQ ID NO 15
<211> LENGTH: 15
<212> TYPE: PRT
<213> ORGANISM: Artificial Sequence
<220> FEATURE:
<223> OTHER INFORMATION: C5a fragment

<400> SEQUENCE: 15

Gln Leu Arg Ala Asn Ile Ser His Lys Asp Met Gln Leu Gly Arg
1               5                   10                  15


<210> SEQ ID NO 16
<211> LENGTH: 8
<212> TYPE: PRT
<213> ORGANISM: Artificial Sequence
<220> FEATURE:
<223> OTHER INFORMATION: C5a fragment

<400> SEQUENCE: 16

His Lys Asp Met Gln Leu Gly Arg
1               5


<210> SEQ ID NO 17
<211> LENGTH: 6
<212> TYPE: PRT
<213> ORGANISM: Artificial Sequence
<220> FEATURE:
<223> OTHER INFORMATION: C5a fragment
```

-continued

<400> SEQUENCE: 17

Asp Met Gln Leu Gly Arg
1 5

<210> SEQ ID NO 18
<211> LENGTH: 5
<212> TYPE: PRT
<213> ORGANISM: Artificial Sequence
<220> FEATURE:
<223> OTHER INFORMATION: C5a fragment

<400> SEQUENCE: 18

Met Gln Leu Gly Arg
1 5

<210> SEQ ID NO 19
<211> LENGTH: 4
<212> TYPE: PRT
<213> ORGANISM: Artificial Sequence
<220> FEATURE:
<223> OTHER INFORMATION: C5a fragment

<400> SEQUENCE: 19

Gln Leu Gly Arg
1

<210> SEQ ID NO 20
<211> LENGTH: 19
<212> TYPE: PRT
<213> ORGANISM: Artificial Sequence
<220> FEATURE:
<223> OTHER INFORMATION: C5a fragment

<400> SEQUENCE: 20

Cys Val Val Ala Ser Gln Leu Arg Ala Asn Ile Ser His Lys Asp Met
1 5 10 15

Gln Leu Gly

<210> SEQ ID NO 21
<211> LENGTH: 14
<212> TYPE: PRT
<213> ORGANISM: Artificial Sequence
<220> FEATURE:
<223> OTHER INFORMATION: C5a fragment

<400> SEQUENCE: 21

Gln Leu Arg Ala Asn Ile Ser His Lys Asp Met Gln Leu Gly
1 5 10

<210> SEQ ID NO 22
<211> LENGTH: 7
<212> TYPE: PRT
<213> ORGANISM: Artificial Sequence
<220> FEATURE:
<223> OTHER INFORMATION: C5a fragment

<400> SEQUENCE: 22

His Lys Asp Met Gln Leu Gly
1 5

<210> SEQ ID NO 23
<211> LENGTH: 6
<212> TYPE: PRT
<213> ORGANISM: Artificial Sequence
<220> FEATURE:
<223> OTHER INFORMATION: C5a fragment -continued

```
<400> SEQUENCE: 23

Lys Asp Met Gln Leu Gly
1               5


<210> SEQ ID NO 24
<211> LENGTH: 10
<212> TYPE: PRT
<213> ORGANISM: Artificial Sequence
<220> FEATURE:
<223> OTHER INFORMATION: C5a fragment

<400> SEQUENCE: 24

Cys Val Val Ala Ser Gln Leu Arg Ala Asn
1               5                   10
```